United States Patent
Kreider et al.

(10) Patent No.: US 11,851,397 B2
(45) Date of Patent: Dec. 26, 2023

(54) METHODS OF MAKING MERCAPTAN COMPOUNDS USING NICKEL-MOLYBDENUM CATALYSTS

(71) Applicant: Chevron Phillips Chemical Company LP, The Woodlands, TX (US)

(72) Inventors: Jason L. Kreider, Copan, OK (US); Daniel M. Hasenberg, Kingwood, TX (US); Brian Gerlach, Borger, TX (US); Dale M. Solaas, Fritch, TX (US); Kenneth M. Lassen, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 17/493,921

(22) Filed: Oct. 5, 2021

(65) Prior Publication Data

US 2022/0106266 A1  Apr. 7, 2022

Related U.S. Application Data

(60) Provisional application No. 63/088,494, filed on Oct. 7, 2020.

(51) Int. Cl.
*C07C 319/08* (2006.01)
*C07C 319/04* (2006.01)
*B01J 23/883* (2006.01)

(52) U.S. Cl.
CPC .......... *C07C 319/08* (2013.01); *C07C 319/04* (2013.01); *B01J 23/883* (2013.01)

(58) Field of Classification Search
CPC ............................ C07C 319/08; C07C 319/04
See application file for complete search history.

(56) References Cited

U.S. PATENT DOCUMENTS

| | | | |
|---|---|---|---|
| 2,402,586 A * | 6/1946 | Alvarado | C07C 319/04 568/65 |
| 3,880,933 A | 4/1975 | Kubicek | |
| 3,963,785 A | 6/1976 | Kubicek | |
| 7,217,843 B2 | 5/2007 | Hasenberg et al. | |
| 7,645,906 B2 | 1/2010 | Hasenberg et al. | |
| 8,008,530 B2 | 8/2011 | Redlingshöfer et al. | |
| 8,765,984 B2 | 7/2014 | Upshaw | |
| 2006/0247475 A1* | 11/2006 | Hasenberg | C07C 319/04 568/72 |
| 2017/0158631 A1 | 6/2017 | Fremy et al. | |

FOREIGN PATENT DOCUMENTS

| | | | |
|---|---|---|---|
| WO | WO-2005040082 A2 * | 5/2005 | B01J 23/28 |
| WO | WO 2008/118925 A2 | 10/2008 | |
| WO | WO 2022/076420 A1 | 4/2022 | |

OTHER PUBLICATIONS

Haldor Topsoe (Manual of Topsoe Hydroprocessing Catalysts, Aug. 2006, 40 pages). (Year: 2006).*
Daniel M. Hasenberg, PhD, "Declaration of Daniel M. Hasenberg, Ph.D," Feb. 2, 2022, 2 pages.
"Hydroprocessing Catalyst Manual: Guides You Through Handling, Loading, Start-up and Operation of Our Hydroprocessing Catalysts." Haldor Topsoe. Nov. 2019. pp. 1-98.
International Search Report and the Written Opinion of the International Searching Authority in PCT/US2021/053581 dated Jan. 24, 2022, 9 pages.

* cited by examiner

*Primary Examiner* — Rosalynd A Keys
(74) *Attorney, Agent, or Firm* — Merchant & Gould P.C.

(57) ABSTRACT

Methods for synthesizing a mercaptan compound include the steps of contacting a nickel-molybdenum catalyst with $H_2S$ at a sulfiding temperature of less than or equal to 235° C. to form a supported sulfur-containing catalyst, and then contacting an alcohol compound or an olefin compound, $H_2S$, and the supported sulfur-containing catalyst to form a reaction mixture containing the mercaptan compound.

22 Claims, No Drawings

METHODS OF MAKING MERCAPTAN COMPOUNDS USING NICKEL-MOLYBDENUM CATALYSTS

REFERENCE TO RELATED APPLICATION

This application claims the benefit of U.S. Provisional Patent Application No. 63/088,494, filed on Oct. 7, 2020, the disclosure of which is incorporated herein by reference in its entirety.

FIELD OF THE INVENTION

The present disclosure relates to processes for producing mercaptan compounds from $H_2S$ and an alcohol or olefin reactant that are contacted in the presence of a supported sulfur-containing nickel-molybdenum catalyst.

BACKGROUND OF THE INVENTION

Mercaptan compounds, also referred to as thiol compounds, can be prepared by various synthesis techniques, but often in relatively low yields or with significant byproducts.

Accordingly, the present invention is generally directed to a catalytic process to produce the mercaptan (or thiol) compound in high yield and with minimal reaction byproducts.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Processes for producing mercaptan compounds are disclosed herein. In one aspect, a first process for producing a mercaptan (or thiol) compound can comprise (i) contacting a nickel-molybdenum catalyst with $H_2S$ at a sulfiding temperature of less than or equal to about 235° C. to form a supported sulfur-containing catalyst, and (ii) contacting an alcohol compound, $H_2S$, and the supported sulfur-containing catalyst to form a reaction mixture comprising the mercaptan compound. In another aspect, a second process for producing a mercaptan compound can comprise (i) contacting a nickel-molybdenum catalyst with $H_2S$ at a sulfiding temperature of less than or equal to about 235° C. to form a supported sulfur-containing catalyst, and (ii) contacting an olefin compound, $H_2S$, and the supported sulfur-containing catalyst to form a reaction mixture comprising the mercaptan compound.

While not limited thereto, the supported sulfur-containing catalyst can contain a solid support, from about 1 to about 5 wt. % nickel, from about 4 to about 18 wt. % molybdenum, and from about 3 to about 18 wt. % sulfur. Additionally, prior to step (ii), the supported sulfur-containing catalyst typically contains less than or equal to about 3 wt. % carbon.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the compounds, compositions, processes, or methods described herein are contemplated with or without explicit description of the particular combination. Additionally, unless explicitly recited otherwise, any aspect or feature disclosed herein can be combined to describe inventive compounds, compositions, processes, or methods consistent with the present disclosure.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

As used herein, a "mercaptan" or "mercaptan" compound is a compound with a —SH group, and also can be referred to herein as a "thiol" compound. The term "hydrocarbon" refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic sub stituents or organic sub stituents as understood by one of ordinary skill in the art.

The terms "contact product," "contacting," and the like, are used herein to describe methods and compositions wherein the components are contacted together in any order, in any manner, and for any length of time, unless otherwise specified. For example, the components can be contacted by blending or mixing. Further, unless otherwise specified, the contacting of any component can occur in the presence or absence of any other component of the methods and compositions described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Consequently, depending upon the circumstances, a "contact product" can be a mixture, a reaction mixture, or a reaction product. Likewise, "contacting" two or more components can result in a reaction product or a reaction mixture.

In this disclosure, while compositions and processes are described in terms of "comprising" various components or steps, the compositions and processes also can "consist essentially of" or "consist of" the various components or steps, unless stated otherwise.

The terms "a," "an," and "the" are intended to include plural alternatives, e.g., at least one. For instance, the disclosure of "a catalyst" is meant to encompass one catalyst, or mixtures or combinations of more than one catalyst, unless otherwise specified.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a moiety is a $C_1$ to $C_{18}$ alkyl group, or in alternative language, an alkyl group having from 1 to 18 carbon atoms, as used herein, refers to a moiety that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ alkyl group), and also including any combination of ranges between these two numbers (for example, a $C_2$ to $C_4$ and a $C_{12}$ to $C_{16}$ alkyl group).

Similarly, another representative example follows for the molar ratio of $H_2S$ to olefin consistent with aspects of this invention. By a disclosure that the molar ratio can be in a range from about 5:1 to about 20:1, the intent is to recite that the molar ratio can be any ratio in the range and, for example, can be equal to about 5:1, about 6:1, about 8:1, about 10:1, about 12:1, about 14:1, about 16:1, about 18:1, or about 20:1. Additionally, the molar ratio can be within any range from about 5:1 to about 20:1 (for example, from about 10:1 to about 15:1), and this also includes any combination of ranges between about 5:1 and about 20:1 (for example, the ratio can be in a range from about 5:1 to about 10:1, or from about 15:1 to about 20:1). Further, in all instances, where "about" a particular value is disclosed, then that value itself is disclosed. Thus, the disclosure of a molar ratio from about 5:1 to about 20:1 also discloses a molar ratio from 5:1 to 20:1 (for example, from 10:1 to 15:1), and this also includes any combination of ranges between 5:1 and 20:1 (for example, the ratio can be in a range from 5:1 to 10:1, or from 15:1 to 20:1). Likewise, all other ranges disclosed herein should be interpreted in a manner similar to these examples.

The term "about" means that amounts, sizes, formulations, parameters, and other quantities and characteristics are not and need not be exact, but can be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, and often within 5% of the reported numerical value.

All disclosed product yields are based on the limiting reactant in the respective reaction, unless explicitly stated otherwise. For example, the limiting reactant in the processes disclosed herein can be the alcohol compound (or the olefin compound) and, therefore, the conversions and yields are based on the initial quantity of the alcohol compound (or the olefin compound).

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are processes for producing mercaptan compounds using sulfur-containing nickel-molybdenum catalysts—at comparable or lower reaction temperatures than for cobalt-molybdenum catalysts—with improved alcohol or olefin conversion, increased mercaptan yield and selectivity, and reduced sulfide by-products.

Synthesizing Mercaptan Compounds

Mercaptan compounds can be produced via two general synthesis schemes. Consistent with some aspects of this invention, a first process to produce the mercaptan compound can comprise (i) contacting a nickel-molybdenum catalyst with $H_2S$ at a sulfiding temperature of less than or equal to about 235° C. to form a supported sulfur-containing catalyst, and (ii) contacting an alcohol compound, $H_2S$, and the supported sulfur-containing catalyst to form a reaction mixture comprising the mercaptan compound. In the first process, the mercaptan compound can have formula (A): $R^1$—SH, the alcohol compound can have formula (B):

$R^1$—OH, and $R^1$ can be a $C_1$ to $C_{18}$ substituted or unsubstituted, cycloalkyl group or linear or branched alkyl group. Consistent with other aspects of this invention, a second process to produce the mercaptan compound can comprise (i) contacting a nickel-molybdenum catalyst with $H_2S$ at a sulfiding temperature of less than or equal to about 235° C. to form a supported sulfur-containing catalyst, and (ii) contacting an olefin compound, $H_2S$, and the supported sulfur-containing catalyst to form a reaction mixture comprising the mercaptan compound. In the second process, the mercaptan compound can have formula (C): $R^2$—SH, the olefin compound can have the formula C=C or formula (D): $R^1$—C=C, $R^1$ can be a $C_1$ to $C_{18}$ substituted or unsubstituted, cycloalkyl group or linear or branched alkyl group, and $R^2$ can be a $C_3$ to $C_{20}$ substituted or unsubstituted, cycloalkyl group or linear or branched alkyl group. As would be recognized by those of skill in the art, the selections for $R^1$ and $R^2$ in the second process are related. For instance, if $R^1$ in formula (D) is a $C_4$ alkyl group, then $R^2$ in formula (C) is a $C_6$ alkyl group.

Generally, the features of the first and second processes for producing mercaptan compounds (e.g., the conditions under which the supported sulfur-containing catalyst is formed, the particular alcohol and olefin reactants, and the conditions under which the mercaptan compound is formed, among others) are independently described herein and these features can be combined in any combination to further describe the disclosed first and second processes to produce a mercaptan compound. Moreover, additional process steps can be performed before, during, and/or after the steps of these processes, and can be utilized without limitation and in any combination to further describe the first and second processes, unless stated otherwise.

Formulas (A), (B), (C), and (D) are not designed to show stereochemistry or isomeric positioning of the different moieties (e.g., these formulas are not intended to show cis or trans isomers), although such compounds are contemplated and encompassed by these formulas. In these formulas, $R^1$ can be a $C_1$ to $C_{18}$ substituted or unsubstituted, cycloalkyl group or linear or branched alkyl group, and $R^2$ can be a $C_3$ to $C_{20}$ substituted or unsubstituted, cycloalkyl group or linear or branched alkyl group. In one aspect, for example, $R^1$ can be a $C_1$ to $C_{14}$ substituted or unsubstituted, cycloalkyl group or linear or branched alkyl group, while in another aspect, $R^1$ can be a $C_1$ to $C_{12}$ substituted or unsubstituted, cycloalkyl group or linear or branched alkyl group, and in yet another aspect, $R^1$ can be a $C_1$ to $C_8$ substituted or unsubstituted, cycloalkyl group or linear or branched alkyl group.

Consistent with aspects of the present invention, $R^1$ and $R^2$ can be a cycloalkyl group; alternatively, $R^1$ and $R^2$ can be a linear alkyl group; or alternatively, $R^1$ and $R^2$ can be a branched alkyl group. Regardless of whether $R^1$ and $R^2$ are a cyclic, linear, or branched alkyl group, $R^1$ and $R^2$ can be unsubstituted, or can be substituted with any suitable substituent, any suitable number of substituents, and at any suitable position(s) that conforms to the rules of chemical valence.

$R^1$ can be a $C_1$ to $C_{18}$ linear or branched alkyl group in certain aspects of this invention. Thus, $R^1$ can be a $C_1$ to $C_{14}$ linear or branched alkyl group, a $C_1$ to $C_{12}$ linear or branched alkyl group, a $C_1$ to $C_8$ linear or branched alkyl group, or a $C_1$ to $C_6$ linear or branched alkyl group. Accordingly, in some aspects, $R^1$ can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a decyl group, or a dodecyl group.

In other aspects, the alkyl group which can be $R^1$ in these formulas can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, a tert-amyl group, a n-hexyl group, a n-heptyl group, a n-octyl group, or a n-dodecyl group; alternatively, a methyl group, an ethyl group, or an iso-propyl group; alternatively, a methyl group or an ethyl group; alternatively, a methyl group; alternatively, an ethyl group; alternatively, a n-propyl group; alternatively, an iso-propyl group; alternatively, a n-butyl group; alternatively, an iso-butyl group; alternatively, a sec-butyl group; alternatively, a tert-butyl group; alternatively, a n-pentyl group; alternatively, an iso-pentyl group; alternatively, a sec-pentyl group; alternatively, a neopentyl group; alternatively, a tert-amyl group; alternatively, a n-hexyl group; alternatively, a n-heptyl group; alternatively, a n-octyl group; or alternatively, or a n-dodecyl group.

$R^1$ can be a cycloalkyl group in other aspects of this invention. Thus, $R^1$ can be a $C_3$ to $C_{18}$ cycloalkyl group, a $C_4$ to $C_{12}$ cycloalkyl group, a $C_4$ to $C_{10}$ cycloalkyl group, or a $C_5$ to $C_8$ cycloalkyl group. Accordingly, in some aspects, $R^1$ in these formulas can be a cyclobutyl group, a cyclopentyl group, a cyclohexyl group, a cycloheptyl group, or a cyclooctyl group; alternatively, a cyclobutyl group; alternatively, a cyclopentyl group; alternatively, a cyclohexyl group; alternatively, a cycloheptyl group; or alternatively, a cyclooctyl group.

In accordance with another aspect of this invention, any alkyl group disclosed herein (cycloalkyl, linear alkyl, or branched alkyl) can be substituted with one or more substituents. Each non-hydrogen substituent(s) for the substituted alkyl group independently can be a $C_1$ to $C_{18}$ hydrocarbyl group; alternatively, a $C_1$ to $C_8$ hydrocarbyl group; or alternatively, a $C_1$ to $C_6$ hydrocarbyl group. Thus, the hydrocarbyl substituent can be a benzyl group, a phenyl group, a tolyl group, or a xylyl group, and the like, and, therefore, $R^1$ and $R^2$ in these formulas can be, for instance, a phenyl-substituted alkyl group. Additionally, the hydrocarbyl substituent can be a $C_1$ to $C_6$ linear or branched alkyl group and, therefore, $R^1$ and $R^2$ in these formulas can be, for instance, an alkyl-substituted cycloalkyl group, such as a methylcyclohexyl group.

Illustrative and non-limiting examples of alcohol compounds that can be used in the first process to produce a mercaptan compound include methanol, ethanol, a propanol, a butanol, a pentanol, a hexanol, a heptanol, an octanol, a nonanol, a decanol, an undecanol, a dodecanol, a tridecanol, a tetradecanol, a pentadecanol, a hexadecanol, a heptadecanol, an octadecanol, cyclopentanol, cyclohexanol, and the like, as well as combinations thereof. Likewise, illustrative and non-limiting examples of olefin compounds that can be used in the second process to produce a mercaptan compound include ethylene, propylene, a butene, a pentene, a hexene, a heptene, an octene, a decene, a dodecene, a tetradecene, a hexadecene, an octadecene, cyclopentene, cyclohexene, and the like, as well as combinations thereof.

Therefore, illustrative and non-limiting examples of mercaptan compounds that can be prepared using the processes disclosed herein can include methyl mercaptan, ethyl mercaptan, isopropyl mercaptan, sec-butyl mercaptan, and the like, as well as combinations thereof.

Step (i) in the first process and the second process for producing a mercaptan compound can comprise contacting a nickel-molybdenum catalyst with $H_2S$ at a sulfiding temperature of less than or equal to about 235° C. to form a supported sulfur-containing catalyst. While not wishing to be bound by theory, it is believed that the nickel-molybdenum catalyst first requires a sulfidation step to form the supported sulfur-containing catalyst, which will then be effective for reacting an alcohol or an olefin compound with $H_2S$ in the presences of the supported sulfur-containing catalyst to form a reaction mixture comprising the mercaptan compound. Herein, it was found that an efficient process for sulfidation of the base catalyst can comprise contacting the nickel-molybdenum catalyst with $H_2S$ at a sulfiding temperature of less than or equal to about 235° C. to form the supported sulfur-containing catalyst, and that this sulfidation step can result in the surprisingly high alcohol/olefin conversions and mercaptan yields disclosed herein.

In step (i), the nickel-molybdenum catalyst can be contacted with $H_2S$ at a sulfiding temperature of less than or equal to about 235° C. to form the supported sulfur-containing catalyst. This sulfidation step can be conducted at any suitable temperature of about 235° C. or below and for any suitable period of time. Representative and non-limiting ranges for the sulfiding temperature in step (i) can include from about 60° C. to about 235° C., from about 40° C. to about 100° C., from about 80° C. to about 225° C., from about 80° C. to about 180° C., from about 110° C. to about 235° C., from about 110° C. to about 200° C., or from about 110° C. to about 160° C. These temperature ranges also are meant to encompass circumstances where step (i) is performed at a series of different temperatures, instead of at a single fixed temperature, falling within the respective temperature ranges, wherein at least one temperature is within the recited ranges.

In an aspect, due to the exothermic nature of the sulfidation, step (i) can comprise contacting the nickel-molybdenum catalyst with inlet $H_2S$ at a very low inlet sulfiding temperature, which can range from about 10° C. to about 90° C., from about 20° C. to about 80° C., from about 20° C. to about 60° C., or from about 35° C. to about 70° C., and the like.

Similarly, the time period for sulfidation step (i) is not particularly limited, and can be conducted for any suitable period of time. In some aspects, the time period can be least about 1 min, at least about 5 min, at least about 10 min, at least about 30 min, at least about 1 hr, at least about 2 hr, at least about 5 hr, or at least about 10 hr. In other aspects, the time period can be from about 30 sec to about 48 hr, from about 1 min to about 24 hr, from about 5 min to about 8 hr, from about 30 min to about 8 hr, or from about 1 hr to about 6 hr.

Step (i) and the sulfidation of the catalyst can be conducted at a sulfiding pressure in a range from about 50 to about 250 psig (344 to 1720 kPag), although not being limited thereto. Other representative and non-limiting ranges for the sulfiding pressure can include from about 50 to about 200 psig (344 to 1379 kPag), from about 100 to about 250 psig (689 to 1720 kPag), from about 100 to about 200 psig (689 to 1379 kPag), or from about 100 to about 150 psig (689 to 1034 kPag).

Generally, before sulfidation, the nickel-molybdenum catalyst is substantially free of sulfur, but after sulfidation in step (i), the supported sulfur-containing catalyst often can contain from about 3 to about 18 wt. % sulfur, such as from about 4 to about 17 wt. %, from about 5 to about 15 wt. %, or from about 7 to about 13 wt. % sulfur. The amount of sulfur is based on the total weight of the supported sulfur-containing catalyst. While not wishing to be bound by theory, it is believed that the sulfidation step is necessary to result in the surprisingly high alcohol/olefin conversions and mercaptan yields disclosed herein.

Optionally, prior to step (i), the nickel-molybdenum catalyst can dried or purged. Thus, the first and second processes to produce a mercaptan compound can further comprise— prior to step (i)—a step of contacting the nickel-molybdenum catalyst with an inert gas at any suitable purging temperature, which often can be less than or equal to about 235° C. For instance, the purging temperature can be in the same temperature ranges as disclosed herein for the sulfiding temperature, such as from about 60° C. to about 200° C., from about 80° C. to about 180° C., or from about 110° C. to about 160° C. In a particular aspect, the purging temperature can be the same as the initial sulfiding temperature, such that the nickel-molybdenum catalyst can be purged and then sulfided immediately thereafter simply be changing the gas stream that contacts the catalyst. In the purging step, any suitable inert gas can be used, such as helium, neon, argon, nitrogen, and the like, as well as any combination thereof. Often, nitrogen is used as the inert gas.

Referring now to step (ii), the appropriate procedure for the contacting (or reacting) in step (ii) in the first process and the second process for producing a mercaptan compound is not particularly limited. For instance, the step of contacting (or reacting) the alcohol compound (or the olefin compound), $H_2S$, and the supported sulfur-containing catalyst can comprise contacting these components in any order that produces an acceptable yield of the desired mercaptan compound. Typically, the alcohol compound (or the olefin compound) and $H_2S$ are combined first, following by contacting the resulting reactant mixture with the supported sulfur-containing catalyst.

The first and second processes to produce the mercaptan compound can be conducted at any suitable temperature and for any suitable period of time. Representative and non-limiting ranges for the temperature of step (ii) (or for the formation of the mercaptan compound) can include from about 100° C. to about 300° C., from about 125° C. to about 275° C., from about 175° C. to about 275° C., from about 175° C. to about 250° C., from about 200° C. to about 300° C., from about 200° C. to about 275° C., or from about 200° C. to about 250° C. These temperature ranges also are meant to encompass circumstances where step (ii) (or the formation of the mercaptan compound) is performed at a series of different temperatures, instead of at a single fixed temperature, falling within the respective temperature ranges, wherein at least one temperature is within the recited ranges.

Similarly, the time period for contacting (or reacting) the alcohol compound (or the olefin compound), $H_2S$, and the supported sulfur-containing catalyst is not particularly limited, and can be conducted for any suitable period of time. In some aspects, the time period can be least about 1 min, at least about 5 min, at least about 10 min, at least about 30 min, at least about 1 hr, at least about 2 hr, at least about 5 hr, or at least about 10 hr. In other aspects, the time period can be from about 30 sec to about 48 hr, from about 1 min to about 24 hr, from about 5 min to about 8 hr, from about 30 min to about 8 hr, or from about 1 hr to about 6 hr.

Often, the first and second processes for forming the mercaptan compound can be a flow process and/or a continuous process. In such circumstances, the alcohol compound (or olefin compound)—catalyst contact time (or reaction time) can be expressed in terms of weight hourly space velocity (WHSV)—the ratio of the weight of the alcohol compound (or olefin compound) which comes in contact with a given weight of catalyst per unit time (units of g/g/hr).

While not limited thereto, the WHSV employed for the processes of producing a mercaptan compound can have a minimum value of 0.01, 0.02, 0.05, 0.1, 0.25, or 0.5; or alternatively, a maximum value of 5, 4, 3, 2.5, 2, or 1. Generally, the WHSV can be in a range from any minimum WHSV disclosed herein to any maximum WHSV disclosed herein. In a non-limiting aspect, the WHSV can be in a range from about 0.01 to about 5; alternatively, from about 0.01 to about 3; alternatively, from about 0.01 to about 1; alternatively, from about 0.02 to about 4; alternatively, from about 0.02 to about 3; alternatively, from about 0.05 to about 2; alternatively, from about 0.05 to about 1.5; alternatively, from about 0.1 to 4; alternatively, from about 0.2 to about 3; alternatively, from about 0.2 to about 1.2; alternatively, from about 0.2 to about 1; alternatively, from about 0.5 to about 4; alternatively, from about 0.5 to about 2; or alternatively, from about 0.5 to about 1. Other WHSV ranges are readily apparent from this disclosure. Any suitable reactor or vessel can be used to form the mercaptan compound, non-limiting examples of which can include a flow reactor, a continuous reactor, a packed tube, and a stirred tank reactor, including more than one reactor in series or in parallel, and including any combination of reactor types and arrangements.

In some aspects of this invention, the first and second processes for producing the mercaptan compound can comprise contacting the alcohol compound (or the olefin compound) and $H_2S$ with a fixed bed of the supported sulfur-containing catalyst.

While not being limited thereto, step (ii) and/or the formation of the mercaptan compound can be conducted at a reaction pressure in a range from about 50 to about 1000 psig (344 to 6890 kPag). Other representative and non-limiting ranges for the reaction pressure can include from about 50 to about 500 psig (344 to 3447 kPag), from about 100 to about 800 psig (689 to 5515 kPag), from about 150 to about 450 psig (1034 to 3103 kPag), from about 200 to about 450 psig (1379 to 3103 kPag), from about 200 to about 350 psig (1379 to 2413 kPag), or from about 300 to about 450 psig (2068 to 3103 kPag).

The molar ratio of $H_2S$:alcohol compound (or $H_2S$:olefin compound) is not particularly limited, so long as the $H_2S$ is used in excess. Typical ranges for molar ratio of $H_2S$:alcohol compound (or $H_2S$:olefin compound) can include, but are not limited to, from about 3:1 to about 50:1, from about 3:1 to about 18:1, from about 3:1 to about 10:1, from about 4:1 to about 30:1, from about 4:1 to about 20:1, from about 5:1 to about 20:1, from about 5:1 to about 15:1, from about 10:1 to about 30:1, or from about 10:1 to about 15:1.

The processes described herein result in an unexpectedly high molar conversion of the alcohol compound or the olefin compound and/or molar yield to the mercaptan compound. In one aspect, the minimum conversion (or yield) can be at least about 50%, at least about 60%, at least about 70%, at least about 80%, at least about 90%, or at least about 95%. Additionally, the maximum conversion (or yield) can be about 97%, about 98%, about 99%, or about 99.5%, and can reach or approach 100% conversion of the alcohol compound or the olefin compound (or yield of the mercaptan). Generally, the conversion (or yield) can be in a range from any minimum conversion (or yield) disclosed herein to any maximum conversion (or yield) disclosed herein. Non-limiting ranges of conversion (or yield) can include from about 50% to about 99.5%, from about 70% to about 95%, from about 80% to about 99%, from about 90% to about 98%, or from about 95% to 100%. For molar conversion, the percentages are the amount of the alcohol compound (or the olefin compound) reactant converted based on the initial amount of the alcohol compound (or the olefin compound). The yield values also are mole percentages, and are based on the moles of the mercaptan compound produced to moles of the alcohol compound (or olefin compound). In some aspects, these conversions (or yields) can be achieved in a batch process, while in other aspects, these conversions (or yields) can be achieved in a flow or continuous process, such as, for example, a single pass or multiple passes through a reactor (e.g., a fixed bed reactor).

Also unexpectedly, continuous flow processes for producing the mercaptan compound in accordance with this invention have unexpectedly high single pass molar conversions of the olefin compound or alcohol compound (or single pass molar yields to the desired mercaptan compound). In one aspect, the minimum single pass conversion (or yield) can be at least about 40%, at least about 50%, at least about 60%, at least about 70%, or at least about 80%. Additionally, the maximum single pass conversion (or yield) can be about 90%, about 95%, about 98%, or about 99%, and can reach or approach 100% conversion of the alcohol compound or the olefin compound (or yield of the mercaptan compound), depending upon the reaction conditions. Generally, the single pass conversion (or yield) can be in a range from any minimum single pass conversion (or yield) disclosed herein to any maximum single pass conversion (or yield) disclosed herein. Non-limiting ranges of single pass conversion (or yield) can include from about 40% to about 90%, from about 50% to about 95%, from about 60% to about 98%, or from about 70% to 100%.

The first and second processes to produce mercaptan compounds disclosed herein typically result in a crude reaction mixture containing the mercaptan compound, residual reactants, and relatively minor amounts of byproducts (e.g., non-mercaptan reaction products such as sulfide heavies). Beneficially, and unexpectedly, the amount of non-mercaptan reaction products (such as sulfides) in the reaction mixture is very low. For instance, in one aspect, the reaction mixture can contain less than or equal to about 15 mol % non-mercaptan reaction products, while in another aspect, the reaction mixture can contain less than or equal to about 10 mol % non-mercaptan reaction products, and in yet another aspect, the reaction mixture can contain less than or equal to about 8 mol % (or 5 mol %, or 3 mol %) non-mercaptan reaction products.

Beneficially, the selectivity of the mercaptan compound in the first process and the second process can be surprisingly high, based on the total amount of mercaptan compounds in the reaction mixture. For instance, the selectivity of the mercaptan compound—based on the total mercaptan compounds—can be at least about 75 mol %; alternatively, at least about 80 mol %; alternatively, at least about 85 mol %; alternatively, at least about 90 mol %; or alternatively, at least about 95 mol %.

In many instances, it can be desirable to isolate the mercaptan compound from the reaction mixture for sale or for use in further industrial processes. Accordingly, in certain aspects, the first process and the second process for producing a mercaptan compound can further comprise a step of isolating the mercaptan compound to form a product stream containing the mercaptan compound. Isolation of the mercaptan compound can employ any suitable technique for separating the mercaptan compound from other components of the reaction mixture, in order to form a product stream containing the mercaptan compound. Such techniques can include, but are not limited to, extraction, filtration, evaporation, or distillation, as well as combinations of two or more of these techniques. In particular aspects of this invention, the isolating step utilizes distillation at any suitable pressure (one or more than one distillation column can be used). Advantageously, the low levels of non-mercaptans in the reaction mixture make isolating, for instance, a mercaptan compound via distillation a relatively straightforward process.

Additionally, other components of the reaction mixture (e.g., unreacted alcohol compound or olefin compound) can be recovered and recycled to the reactor after step (ii). In such instances, the alcohol compound or the olefin compound can be recycled to extinction, such that all or substantially all (>99 mol %) of the alcohol compound or olefin compound reactant is converted to the mercaptan compound or to a byproduct.

Catalysts

The nickel-molybdenum catalyst and the supported sulfur-containing catalyst can contain any suitable solid support, encompassing any suitable solid oxide or like material. Illustrative examples of solid supports can include silica, alumina (e.g., γ-alumina), magnesia, boria, titania, zirconia, a zeolite, and the like, as well as mixed oxides thereof (e.g., silica-alumina). Combinations of more than one support material can be used for the catalyst.

If used, the Y-zeolite (zeolite Y) and X-zeolite (zeolite X) can have an average pore diameter in a range of from about 7 Å to about 12 Å. The Si:Al ratio for a X-zeolite is less than that for a Y-zeolite. Often, the zeolite can be bound with a support matrix (or binder), non-limiting examples of which can include silica, alumina, magnesia, boria, titania, zirconia, various clays, and the like, including mixed oxides thereof, as well as mixtures thereof.

The amount of nickel present in the nickel-molybdenum catalyst and the supported sulfur-containing catalyst is not particularly limited, but often ranges from about 1 to about 5 wt. %. In one aspect, the amount of nickel can be from about 1 to about 3 wt. %, while in another aspect, the amount of nickel can be from about 2 to about 5 wt. %, and in yet another aspect, the amount of nickel can be from about 2 to about 4 wt. %, and in still another aspect, the amount of nickel can be from about 2.5 to about 4 wt. %. These weight percentages are based on the amount of nickel relative to the total weight of the nickel-molybdenum catalyst or the supported sulfur-containing catalyst.

Likewise, the amount of molybdenum on the catalysts is not particularly limited, and typically ranges from about 4 to about 18 wt. %. In some aspects, the nickel-molybdenum catalyst and the supported sulfur-containing catalyst can contain from about 4 to about 16 wt. %; alternatively, from about 10 to about 15 wt. %; alternatively, from about 11 to about 17 wt. %; or alternatively, from about 13 to about 16 wt. % molybdenum, based on the total weight of the respective catalyst. While not wishing to be bound by theory, it is believed that a higher molybdenum loading improves conversion and/or yield.

Generally, prior to use, the nickel-molybdenum catalyst and the supported sulfur-containing catalyst contain little to no carbon, for example, less than or equal to about 3 wt. %. More often, the respective catalysts can contain less than or equal to about 2.5 wt. % carbon, less than or equal to about 2 wt. % carbon, less than or equal to about 1 wt. % carbon, or less than or equal to about 0.5 wt. % carbon. As above, these weight percentages are based on the total weight of the respective nickel-molybdenum catalyst or supported sulfur-containing catalyst.

While the nickel-molybdenum catalyst contains substantially no sulfur prior to sulfidation, the supported sulfur-containing catalyst (after sulfidation) often contains at least about 3 wt. % sulfur and less than or equal to about 18 wt. % sulfur. Illustrative and non-limiting ranges for the amount of sulfur on the supported sulfur-containing catalyst include from about 4 to about 17 wt. %, from about 5 to about 15 wt. %, from about 7 to about 13 wt. % sulfur, and the like. These weight percentages are based on the total weight of the supported sulfur-containing catalyst. While not wishing to be bound by theory, it is believed that an appropriate level of sulfur is necessary to result in the surprisingly high alcohol/olefin conversions and mercaptan yields disclosed herein.

The nickel-molybdenum catalyst and the supported sulfur-containing catalyst can have any suitable BET surface area, including surface areas from about 75 to about 400 $m^2/g$, from about 100 to about 350 $m^2/g$, from about 100 to about 300 $m^2/g$, from about 125 to about 275 $m^2/g$, from about 150 to about 375 $m^2/g$, or from about 150 to about 250 $m^2/g$.

The nickel-molybdenum catalyst and the supported sulfur-containing catalyst can have any suitable shape or form, and such can depend on the type of process that is employed to convert the alcohol or olefin reactant into the mercaptan compound (e.g., fixed bed versus fluidized bed). Illustrative and non-limiting shapes and forms include powder, round or spherical (e.g., a sphere), ellipsoidal, pellet, bead, cylinder, granule (e.g., regular and/or irregular), trilobe, quadrilobe, ring, wagon wheel, monolith, and the like, as well as any combination thereof. Accordingly, various methods can be utilized to prepare the supported catalyst particles, including, for example, extrusion, spray drying, pelletizing, marumerizing, spherodizing, agglomeration, oil drop, and the like, as well as combinations thereof.

In some aspects, the nickel-molybdenum catalyst and the supported sulfur-containing catalyst can be in the form of pellets or beads—and the like—having an average particle size (or average diameter) ranging from about 0.5 to about 15 mm, from about 1 to about 7 mm, or from about 2.5 to about 5 mm. As noted above, the size of the nickel-molybdenum catalyst and the supported sulfur-containing catalyst particles can be varied to suit the particular process for converting the alcohol or olefin reactant into the mercaptan compound.

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

These examples demonstrate that the sulfur-containing nickel molybdenum catalysts utilized herein provided both better activity and selectivity for the production of mercaptans from $H_2S$ and either olefins or alcohols than when using cobalt molybdenum catalysts. In addition, the increased conversions and mercaptan product yields (e.g., increases of 5-10%) were obtained at significantly less severe operating conditions (i.e., lower reaction temperatures, higher hydrocarbon space velocities, and lower $H_2S$:olefin or $H_2S$:alcohol feed ratios).

Examples 1-2

In Examples 1-2, methyl mercaptan (MeSH) was synthesized from methanol (MeOH) and $H_2S$. One mole of water is produced for each mole of methanol that reacts. Methanol can react further (e.g., with MeSH) to form dimethyl sulfide (DMS) and water. Higher temperatures generally favor DMS production over MeSH. Herein, MeSH is the desirable product. Additionally, methanol (and MeSH) can decompose to form $CO_2$ (and $CS_2$) and hydrogen, and higher temperatures increase the rate of these unwanted decomposition reactions.

Examples 1-2 used a 1-inch stainless steel reactor in downflow, and catalysts were diluted with 14-20 mesh Alundum® in order to help establish isothermal reactor operation. A ¼-inch centerline thermowell with three thermocouples was used for temperature measurement, and the reaction temperature (Temp) was the arithmetic average of the three temperatures (note that the temperatures of the three thermocouples were ordinarily within 2° C. of each other).

Analysis of the reaction mixture was conducted using an on-line HP-6580 gas chromatograph equipped with a thermal conductivity detector. The temperature profile was a 35° C. hold for 5 min, then ramping at 5° C./min to 70° C., followed by ramping at 15° C./min to 260° C. and holding for 10 min. The column was a CP-Sil 5CB for sulfur, 30 m×320 μm×4 μm, and 0.5 mL/min He flow. The detector was operated at 200° C., and the response factors used for this detector were: $CO_2$ 0.92; $H_2S$ 0.88; $H_2O$ 0.55; dimethyl ether (DME) 0.67; MeOH 0.58; MeSH 0.81; $CS_2$ 0.82; DMS 0.80; and dimethyl disulfide (DMDS) 0.80.

For Example 1, Table 1 summarizes the experimental results for the synthesis of methyl mercaptan from methanol and $H_2S$ using a cobalt molybdate catalyst (CoMo, 3 wt. % Co and 11 wt. % Mo, fresh catalyst basis) at a 7.6:1 $H_2S$:methanol molar feed ratio, while Table 2 summarizes results at a 10.8:1 $H_2S$:methanol molar feed ratio, and Table 3 summarizes results at a 15.5:1 $H_2S$:methanol molar feed ratio. MeSH yield is defined as the product of methanol conversion and selectivity to methyl mercaptan.

The results from Example 1 show that a minimum temperature of least 240° C. was necessary for 99 mol % methanol conversion using cobalt molybdate catalysts, but the maximum MeSH yield (product of conversion and selectivity) occurred between 220 and 230° C. A level of 99 mol % methanol conversion was not obtained at a 7.6:1 feed ratio at any temperature at or below 240° C., and one hundred percent methanol conversion was not observed at any temperature at or below 240° C. The higher feed molar ratio of 15.5:1 resulted in greater selectivity to MeSH than at the 10.8:1 feed ratio, which in turn gave greater MeSH yield than at the 7.6:1 ratio.

The highest methyl mercaptan yield obtained was 89-90 mol % (15.5:1 feed ratio and 220° C.), although at these conditions, methanol conversion was less than 99 mol %. The highest methyl mercaptan yield while obtaining at least 99% methanol conversion was 88.8 mol % yield (15.5:1 feed ratio and 240° C.).

For Example 2, Table 4 summarizes the experimental results for the synthesis of methyl mercaptan from methanol and $H_2S$ using a nickel molybdate catalyst (NiMo, 3 wt. % Ni and 10-11 wt. % Mo, fresh catalyst basis) at a 9.9:1 $H_2S$:methanol feed ratio, while Table 5 summarizes results at a 14.8:1 $H_2S$:methanol feed ratio, and Table 6 summarizes results at a 17.1:1 $H_2S$:methanol feed ratio. MeSH yield is defined as the product of methanol conversion and selectivity to methyl mercaptan.

The results from Example 2 show that substantially complete (>99 mol %) methanol conversion was achieved at 220° C. (or greater) using the NiMo catalyst of Example 2 in contrast to the 240° C. necessary when using the CoMo catalyst of Example 1. Further, 100 mol % methanol conversion in Example 2 was achieved at 230° C. or greater (at feed ratios above 14:1), in contrast to the CoMo catalyst of Example 1, in which 100 mol % methanol conversion was not observed at any temperature. Similar to Example 1, higher molar $H_2S$/methanol feed ratios resulted in increased MeSH selectivity in Example 2. However, the NiMo catalyst of Example 2 gave MeSH yields of 91.8 mol % (at >99 mol % methanol conversion), which were not obtained using the CoMo catalyst of Example 1 (MeSH yield of 88.8 mol % at >99 mol % methanol conversion).

Additionally, operating at or near 100% methanol conversion, as in Example 2 using the NiMo catalyst, is desirable since it eliminates the need for downstream separation or purification to remove or recycle unreacted methanol. Methanol can be difficult to remove from the product MeSH, because methanol does not form a lower boiling azeotrope with water. Typically, the methanol concentration often must be below 400 ppmw in commercial MeSH products.

Examples 3-4

In Examples 3-4, isopropyl mercaptan (IPM, 2-propanethiol) was synthesized from propylene and $H_2S$. Examples 3-4 were performed and analyzed in a manner similar to that of Examples 1-2, except a jacketed 6-inch ID 5% chrome steel reactor in downflow was used, and temperatures of the inlet feed and the effluent reaction mixture were measured by thermocouples, with the reaction temperature (Temp) being the arithmetic average of the inlet and outlet temperatures.

Analysis of the reaction mixture was conducted using an Agilent 6850A gas chromatograph equipped with an Agilent G2613A liquid autosampler. The GC was equipped with a thermal conductivity detector operating at 300° C. The temperature profile was a 50° C. hold for 1.5 min, then ramping at 20° C./min to 100° C., followed by ramping at 50° C./min to 275° C., and holding for 1.5 min. The column was a DB-1 (standard polysiloxane), 15 m×320 μm×1 μm, 0.8 mL/min $H_2$ flow, operated in ramped flow mode.

For Example 3, Table 7 summarizes the experimental results for the synthesis of IPM from propylene and $H_2S$ using a cobalt molybdate catalyst (CoMo, 3 wt. % Co and 10-11 wt. % Mo, fresh catalyst basis) at a 9:1-11:1 $H_2S$:propylene molar feed ratio, a reaction pressure of 330 psig, and a feed rate of 0.6-0.7 WHSV based on propylene. In Table 7, the composition of the reaction mixture as a function of temperature is shown, where isopropyl mercaptan (IPM), normal propyl mercaptan (NPM), and undesirable heavies (sulfides such as di-normal propyl sulfide, or isopropyl-normal propyl sulfide) are the primary products.

From Table 7, the highest yield of IPM in the reactor effluent was 78.4 mol % using the CoMo catalyst, while the typical yields were several percentage points less. The highest combined yield of IPM and NPM was 87.4 mol %. To achieve these results, reactor temperatures of about 400° F. and above were required. Under these conditions, the average amount of sulfides was 10.6 mol %, and unreacted propylene ranged from 0.4 to 1.2 mol %.

For Example 4, Table 8 summarizes the experimental results for the synthesis of IPM from propylene and $H_2S$ using a nickel molybdate catalyst (NiMo, 3.4 wt. % Ni and 14 wt. % Mo, fresh catalyst basis) at a 8.8:1 $H_2S$:propylene molar feed ratio, a reaction pressure of 330 psig, and a feed rate of 0.73 WHSV based on propylene. In Table 8, the composition of the reaction mixture as a function of temperature is shown, where isopropyl mercaptan (IPM), normal propyl mercaptan (NPM), and undesirable heavies (sulfides such as di-normal propyl sulfide, or isopropyl-normal propyl sulfide) are the primary products.

For Example 4, Table 9 also summarizes the experimental results for the synthesis of IPM from propylene and $H_2S$ using a nickel molybdate catalyst (NiMo, 3.4 wt. % Ni and 14 wt. % Mo, fresh catalyst basis) at a 6:1-8:1 $H_2S$:propylene molar feed ratio, a reaction pressure of 330 psig, and a feed rate of 0.8-0.9 WHSV based on propylene. In Table 9, the composition of the reaction mixture as a function of temperature is shown, where isopropyl mercaptan (IPM), normal propyl mercaptan (NPM), and undesirable heavies (sulfides such as di-normal propyl sulfide, or isopropyl-normal propyl sulfide) are the primary products.

From Tables 8-9, the highest yield of IPM in the reactor effluent was 88.2 mol % using the NiMo catalyst, while the typical yields were above 85 mol %. The highest combined yield of IPM and NPM was 96.2 mol %. To achieve these results, reactor temperatures of only about 365-380° F. were used. Under these conditions, the average amount of sulfides was less than 5 mol %, and unreacted propylene ranged was 0.1 mol % or less.

Comparing Example 3 (CoMo) and Example 4 (NiMo), the highest yield of IPM (88.2 mol %) in Example 4 was 9.8 mol % greater than the highest IPM yield in Example 3, and this was achieved at a 30° F. lower temperature using the NiMo catalyst in Example 4. Further, the amount of unreacted propylene in Example 4 was 0.1 mol % or less in the reactor mixture, while operating at up to 20% greater space velocities and at as much as 27° F. lower temperatures with the nickel molybdate catalyst in Example 4 as compared to the cobalt molybdate catalyst in Example 3.

The amount of unwanted sulfides was always lower using the NiMo catalyst (maximum of 7.4%) in contrast to a minimum of 8.8% with the CoMo catalyst. The lower reactor temperatures necessary for increased IPM production allowed for a reduction of about half in sulfides formation while using the NiMo catalyst. This combination of both a higher product yield and higher propylene conversion while operating at a lower reaction temperature is a significant and unexpected advantage for isopropyl mercaptan synthesis using the NiMo catalyst as compared to the CoMo catalyst.

Examples 5-6

In Examples 5-6, sec-butyl mercaptan (SBM, 2-butanethiol) was synthesized from 1-butene and $H_2S$. Examples 5-6 were performed and analyzed in the same manner as Examples 3-4. Analysis of the reaction mixture was conducted using an Agilent 6850A gas chromatograph equipped with an Agilent G2613A liquid autosampler. The GC was equipped with a flame ionization detected operating at 300° C. The temperature profile was a 35° C. hold for 1.8 min, then ramping at 30° C./min to 250° C., and holding for 2 min. The column was a DB-1 (standard polysiloxane), 30 m×320 μm×0.25 μm, 1.5 mL/min $H_2$ flow, operated in ramped pressure mode.

For Examples 5-6, Table 10 summarizes the experimental results for the synthesis of SBM from 1-butene and $H_2S$ using a cobalt molybdate catalyst (CoMo, 3 wt. % Co and 10 wt. % Mo, fresh catalyst basis, Example 5A and Example 5B) and using a nickel molybdate catalyst (NiMo, 3.4 wt. % Ni and 14 wt. % Mo, fresh catalyst basis, Example 6). In Table 10, the composition of the reaction mixture and the reaction temperature are shown, where sec-butyl mercaptan (SBM), normal butyl mercaptan (NBM), and undesirable heavies (sulfides such as di-normal butyl sulfide, di-sec-butyl sulfide, and secondary-normal sulfides) are the primary products. The WHSV values were based on 1-butene.

Using the CoMo catalyst in Examples 5A and 5B, the highest yield of SBM in the reaction mixture was 73.7 wt. %, with the average SBM yield of 71.5 wt. % and mercaptan yield of 81.5 wt. %. Reaction temperature was 404° F., which resulted in 8-12 wt. % sulfides and over 6 wt. % unreacted 1-butene. Using the NiMo catalyst in Example 6, the yield of SBM in the reaction mixture was surprisingly 10 wt. % greater than the average yield in Example 5, and this was achieved at a 33° F. lower temperature. Sulfides were reduced by 2-5 wt. % and unreacted butene was reduced by 1 wt. %, while a 15% greater space velocity was used and a 32% lower $H_2S$:butene feed ratio.

Example 7

Example 7 summarizes the pre-sulfiding or sulfidation of the base catalyst with $H_2S$. Sulfiding of catalysts for use in mercaptan synthesis cannot be done using diesel hydrocarbons due to product purity concerns for synthesis and manufacture of mercaptan products, and further, most refineries do not have $H_2S$ available at pressures greater than about 30 psig. The base NiMo catalysts used in Examples 3-6 were sulfided using $H_2S$ at a pressure above 100 psig. The use of high pressure $H_2S$ moderated the temperature increase during the exothermic catalyst sulfiding reactions (e.g., $MoO_2 + 2H_2S \rightarrow MoS_2 + 2H_2O$). Isothermal conditions are typically desired during sulfiding in order to maximize catalyst activity and effectiveness.

Prior to sulfidation, the base NiMo catalyst was purged in nitrogen at 120-150° C. for approximately 10 hr, then pre-sulfided using a gas stream of $H_2S$ at a pressure at or above 100 psig (but less than 250 psig) for less than 24 hr, resulting in approximately 10-11 wt. % sulfur on the sulfided catalyst. The time and temperature data during a typical pre-sulfiding experiment are presented in Table 11. The maximum temperature recorded during sulfiding was 283° F., although the maximum weight average sulfiding temperature was 184° F. The amount of reactor pre-heat was reduced for two hours at the time of this temperature spike to help mitigate the extent of the temperature increase. After the temperature started to increase in the reactor, the feed rate of $H_2S$ was also reduced for several hours to help mitigate the temperature increase in the reactor.

Examples 8-9

In Examples 8-9, ethyl mercaptan (ethanethiol) was synthesized from ethylene and $H_2S$. Examples 8-9 were performed and analyzed in the same manner as Examples 5-6, except that a jacketed tubular reactor with 2-inch stainless steel pipes in downflow was used, and temperatures of the inlet feed and the effluent reaction mixture were measured by thermocouples, with the reaction temperature (Temp) being the arithmetic average of the inlet and outlet temperatures. Analysis of the effluent reaction mixture was conducted using an on-line gas chromatograph equipped with a flame ionization detector. Key components of the effluent reaction mixture were the desired product, ethyl mercaptan (ethanethiol), and undesired sulfide heavies including diethyl sulfide and diethyl disulfide.

For Examples 8-9, Table 12 summarizes the experimental results for the synthesis of ethyl mercaptan from ethylene and $H_2S$ using a cobalt molybdate catalyst (CoMo, 3 wt. % Co and 11 wt. % Mo, fresh catalyst basis, Example 8) and using a nickel molybdate catalyst (NiMo, 3.4 wt. % Ni and 14 wt. % Mo, fresh catalyst basis, Example 9). Sulfidation was performed as described in Example 7. In Table 12, the composition of the reaction mixture and the reaction temperature are shown, where ethyl mercaptan and undesirable heavies (sulfides such as diethyl sulfide and diethyl disulfide) are the primary products. The WHSV values were based on ethylene, and the molar ratios of $H_2S$:ethylene were 5.1-5.2 to 1.

From Table 12, the maximum attainable ethyl mercaptan concentration in the reactor effluent was 5.6 wt. % greater when the NiMo catalyst (Example 9) was used as compared to the CoMo catalyst (Example 8). While operating at the same reactor pressure, ethylene space velocity, and $H_2S$:ethylene ratio, the reaction temperature was 43° C. lower when the NiMo catalyst was used, while concurrently attaining the maximum ethyl mercaptan conversion (99.9+ wt. %) across the reactor outlet as compared to the CoMo catalyst.

This lower reaction temperature is a substantial operational advantage in that it decreases both the amount of required reactor pre-heat as well as the pre-heat supply temperature. Moreover, the lower operating temperature also resulted in a 44% decrease in production of unwanted sulfides and disulfides. This reduced amount of sulfides and disulfides was not attained at any reactor conditions using the CoMo catalyst while converting greater than 90 wt. % of the ethylene on a one-pass basis.

Beneficially, the NiMo catalyst used in Example 9 provided both a substantial increase in catalyst activity and yield. Referring to activity, the exceptional NiMo catalyst activity resulted in greater than 99.9 wt. % ethylene conversion at a temperature 43° C. lower than for the CoMo catalyst (at its highest ethylene conversion, which was only 96.5 wt. %), at otherwise identical reactor operating conditions. Referring to yield, Example 9 using the NiMo catalyst achieved 97.1 wt. % yield of ethyl mercaptan, which also was unexpectedly higher than that achieved with the CoMo catalyst in Example 8.

TABLE 1

| $H_2S$/MeOH mole ratio | Pressure psig | WHSV | Temp ° C. | $CO_2$ Mol % | $H_2S$ Mol % | $H_2O$ Mol % | MeOH Mol % | MeSH Mol % | DMS Mol % | DMDS Mol % | MeOH Conversion % | MeSH Selectivity % | MeSH Yield % |
|---|---|---|---|---|---|---|---|---|---|---|---|---|---|
|  |  | Feed |  | 0.00 | 88.08 | 0.37 | 11.55 | 0.00 | 0.00 | 0.00 |  |  |  |
| 7.6 | 450 | 0.25 | 180.0 | 0.00 | 86.71 | 2.07 | 6.67 | 4.39 | 0.10 | 0.00 | 42.26 | 95.66 | 40.42 |
| 7.6 | 450 | 0.25 | 180.0 | 0.00 | 85.21 | 3.02 | 7.28 | 4.34 | 0.09 | 0.00 | 36.95 | 96.20 | 35.55 |
| 7.6 | 450 | 0.25 | 190.0 | 0.00 | 85.65 | 2.55 | 5.62 | 5.96 | 0.13 | 0.00 | 51.32 | 95.78 | 49.16 |
| 7.6 | 450 | 0.25 | 200.3 | 0.00 | 84.90 | 2.13 | 4.42 | 8.19 | 0.24 | 0.02 | 61.70 | 94.08 | 58.05 |
| 7.6 | 450 | 0.25 | 210.7 | 0.05 | 84.56 | 1.75 | 3.15 | 10.00 | 0.39 | 0.02 | 72.71 | 92.07 | 66.94 |
| 7.6 | 450 | 0.25 | 210.3 | 0.00 | 84.97 | 1.60 | 2.43 | 10.43 | 0.45 | 0.00 | 78.99 | 92.12 | 72.76 |
| 7.6 | 450 | 0.25 | 220.3 | 0.07 | 85.04 | 1.05 | 0.61 | 12.36 | 0.79 | 0.00 | 94.74 | 88.21 | 83.56 |
| 7.6 | 450 | 0.25 | 220.3 | 0.09 | 85.21 | 0.96 | 0.59 | 12.33 | 0.77 | 0.00 | 94.90 | 88.38 | 83.87 |
| 7.6 | 450 | 0.25 | 229.7 | 0.12 | 84.95 | 0.98 | 0.52 | 12.37 | 1.06 | 0.00 | 95.54 | 84.64 | 80.86 |
| 7.6 | 450 | 0.25 | 230.0 | 0.13 | 84.88 | 1.00 | 0.43 | 12.42 | 1.16 | 0.00 | 96.27 | 83.56 | 80.44 |
| 7.6 | 450 | 0.25 | 240.0 | 0.18 | 85.75 | 0.97 | 0.18 | 11.50 | 1.55 | 0.00 | 98.44 | 77.85 | 76.64 |
| 7.6 | 450 | 0.25 | 240.0 | 0.19 | 85.93 | 0.95 | 0.14 | 11.32 | 1.60 | 0.00 | 98.77 | 76.96 | 76.01 |

TABLE 2

| $H_2S$/MeOH mole ratio | Press psig | WHSV | Temp ° C. | $CO_2$ Mol % | $H_2S$ Mol % | $H_2O$ Mol % | MeOH Mol % | MeSH Mol % | DMS Mol % | DMDS Mol % | MeOH Conversion % | MeSH Selectivity % | MeSH Yield % |
|---|---|---|---|---|---|---|---|---|---|---|---|---|---|
|  |  | Feed |  | 0.00 | 91.32 | 0.25 | 8.43 | 0.00 | 0.00 | 0.00 |  |  |  |
| 10.8 | 450 | 0.25 | 159.7 | 0.00 | 90.66 | 1.03 | 6.50 | 1.73 | 0.03 | 0.01 | 22.89 | 91.78 | 21.01 |
| 10.8 | 450 | 0.25 | 159.7 | 0.00 | 90.21 | 1.13 | 6.90 | 1.68 | 0.03 | 0.00 | 18.18 | 91.45 | 16.62 |
| 10.8 | 450 | 0.25 | 170.0 | 0.00 | 89.64 | 1.25 | 6.79 | 2.23 | 0.04 | 0.01 | 19.50 | 91.93 | 17.93 |
| 10.8 | 450 | 0.25 | 170.0 | 0.00 | 89.88 | 1.37 | 6.20 | 2.44 | 0.04 | 0.01 | 26.42 | 92.38 | 24.41 |
| 10.8 | 450 | 0.25 | 180.3 | 0.00 | 88.91 | 1.62 | 5.90 | 3.43 | 0.05 | 0.01 | 29.97 | 92.76 | 27.80 |
| 10.8 | 450 | 0.25 | 180.0 | 0.00 | 89.36 | 1.68 | 5.18 | 3.64 | 0.06 | 0.01 | 38.59 | 92.83 | 35.82 |
| 10.8 | 450 | 0.25 | 190.0 | 0.03 | 88.98 | 1.80 | 4.28 | 4.76 | 0.08 | 0.01 | 49.21 | 92.35 | 45.45 |
| 10.8 | 450 | 0.25 | 190.0 | 0.03 | 89.32 | 1.72 | 3.94 | 4.84 | 0.08 | 0.01 | 53.31 | 92.24 | 49.18 |
| 10.8 | 450 | 0.25 | 200.0 | 0.04 | 86.49 | 1.51 | 3.28 | 5.96 | 0.12 | 0.01 | 61.12 | 51.71 | 31.61 |
| 10.8 | 450 | 0.25 | 200.0 | 0.04 | 88.96 | 1.36 | 2.78 | 6.63 | 0.14 | 0.01 | 67.04 | 91.84 | 61.57 |
| 10.8 | 450 | 0.25 | 209.7 | 0.06 | 88.39 | 0.83 | 1.06 | 9.30 | 0.28 | 0.01 | 87.46 | 91.07 | 79.66 |
| 10.8 | 450 | 0.25 | 209.7 | 0.07 | 88.59 | 0.88 | 1.06 | 9.04 | 0.26 | 0.01 | 87.38 | 90.79 | 79.33 |
| 10.8 | 450 | 0.25 | 220.0 | 0.08 | 87.74 | 0.97 | 1.45 | 9.40 | 0.28 | 0.01 | 82.83 | 90.62 | 75.06 |
| 10.8 | 450 | 0.25 | 219.7 | 0.08 | 87.61 | 0.97 | 1.36 | 9.83 | 0.06 | 0.01 | 83.88 | 94.79 | 79.52 |
| 10.8 | 450 | 0.25 | 220.0 | 0.09 | 87.42 | 0.88 | 1.07 | 10.12 | 0.34 | 0.01 | 87.36 | 90.07 | 78.68 |
| 10.8 | 450 | 0.25 | 229.7 | 0.11 | 87.65 | 0.81 | 0.59 | 10.39 | 0.40 | 0.01 | 93.01 | 89.38 | 83.14 |
| 10.8 | 450 | 0.25 | 230.0 | 0.13 | 87.70 | 0.75 | 0.49 | 10.45 | 0.45 | 0.01 | 94.19 | 88.68 | 83.53 |
| 10.8 | 450 | 0.25 | 230.0 | 0.14 | 87.70 | 0.85 | 0.34 | 10.48 | 0.49 | 0.00 | 95.96 | 88.18 | 84.61 |

TABLE 2-continued

| H$_2$S/MeOH mole ratio | Press psig | WHSV | Temp ° C. | CO$_2$ Mol % | H$_2$S Mol % | H$_2$O Mol % | MeOH Mol % | MeSH Mol % | DMS Mol % | DMDS Mol % | MeOH Conversion % | MeSH Selectivity % | MeSH Yield % |
|---|---|---|---|---|---|---|---|---|---|---|---|---|---|
| 10.8 | 450 | 0.25 | 240.0 | 0.17 | 87.74 | 0.72 | 0.13 | 10.70 | 0.59 | 0.00 | 98.45 | 87.13 | 85.78 |
| 10.8 | 450 | 0.25 | 240.3 | 0.19 | 87.78 | 0.70 | 0.08 | 10.67 | 0.67 | 0.00 | 99.00 | 86.15 | 85.29 |
| 10.8 | 450 | 0.25 | 240.0 | 0.20 | 88.00 | 0.72 | 0.06 | 10.46 | 0.68 | 0.00 | 99.28 | 85.91 | 85.29 |

TABLE 3

| H$_2$S/MeOH mole ratio | Pressure psig | WHSV | Temp ° C. | CO$_2$ Mol % | H$_2$S Mol % | H$_2$O Mol % | MeOH Mol % | MeSH Mol % | DMS Mol % | DMDS Mol % | MeOH Conversion % | MeSH Selectivity % | MeSH Yield % |
|---|---|---|---|---|---|---|---|---|---|---|---|---|---|
|  |  |  | Feed | 0.00 | 93.55 | 0.30 | 6.15 | 0.00 | 0.00 | 0.00 |  |  |  |
| 15.5 | 450 | 0.25 | 210.0 | 0.05 | 91.04 | 1.04 | 1.52 | 6.11 | 0.13 | 0.01 | 75.27 | 92.06 | 69.29 |
| 15.5 | 450 | 0.25 | 210.0 | 0.06 | 91.19 | 0.96 | 1.31 | 6.24 | 0.14 | 0.01 | 78.74 | 92.01 | 72.45 |
| 15.5 | 450 | 0.25 | 210.0 | 0.06 | 91.26 | 0.87 | 0.98 | 6.57 | 0.15 | 0.01 | 84.11 | 91.96 | 77.34 |
| 15.5 | 450 | 0.25 | 219.7 | 0.09 | 90.93 | 0.61 | 0.09 | 7.96 | 0.23 | 0.00 | 98.61 | 91.46 | 90.19 |
| 15.5 | 450 | 0.25 | 220.0 | 0.10 | 91.27 | 0.61 | 0.11 | 7.59 | 0.22 | 0.00 | 98.20 | 91.18 | 89.54 |
| 15.5 | 450 | 0.25 | 220.3 | 0.09 | 91.31 | 0.64 | 0.15 | 7.48 | 0.22 | 0.00 | 97.57 | 90.91 | 88.70 |
| 15.5 | 450 | 0.25 | 230.0 | 0.10 | 90.82 | 0.71 | 0.32 | 7.71 | 0.23 | 0.00 | 94.79 | 90.82 | 86.09 |
| 15.5 | 450 | 0.25 | 229.7 | 0.11 | 91.51 | 0.72 | 0.23 | 7.11 | 0.23 | 0.00 | 96.19 | 90.55 | 87.10 |
| 15.5 | 450 | 0.25 | 230.0 | 0.12 | 91.08 | 0.75 | 0.14 | 7.56 | 0.26 | 0.00 | 97.73 | 90.40 | 88.35 |
| 15.5 | 450 | 0.25 | 240.0 | 0.14 | 91.36 | 0.73 | 0.05 | 7.36 | 0.31 | 0.00 | 99.24 | 89.49 | 88.80 |
| 15.5 | 450 | 0.25 | 240.0 | 0.16 | 91.39 | 0.72 | 0.03 | 7.32 | 0.34 | 0.00 | 99.49 | 88.81 | 88.37 |

TABLE 4

| H$_2$S/MeOH mole ratio | Press psig | WHSV | Temp ° C. | CO$_2$ Mol % | H$_2$S Mol % | H$_2$O Mol % | MeOH Mol % | MeSH Mol % | DMS Mol % | DMDS Mol % | MeOH Conversion % | MeSH Selectivity % | MeSH Yield % |
|---|---|---|---|---|---|---|---|---|---|---|---|---|---|
|  |  |  | Feed | 0.00 | 90.21 | 0.66 | 9.14 | 0.00 | 0.00 | 0.00 |  |  |  |
| 9.9 | 450 | 0.25 | 199.7 | 0.00 | 87.66 | 1.04 | 1.56 | 9.25 | 0.31 | 0.12 | 82.96 | 90.45 | 75.04 |
| 9.9 | 450 | 0.25 | 199.7 | 0.02 | 86.68 | 0.96 | 1.25 | 10.49 | 0.44 | 0.13 | 86.28 | 88.99 | 76.78 |
| 9.9 | 450 | 0.25 | 199.7 | 0.02 | 87.20 | 0.88 | 1.02 | 10.30 | 0.43 | 0.11 | 88.86 | 89.14 | 79.21 |
| 9.9 | 450 | 0.25 | 209.7 | 0.03 | 86.74 | 0.91 | 1.09 | 10.61 | 0.51 | 0.09 | 88.05 | 88.64 | 78.04 |
| 9.9 | 450 | 0.25 | 210.0 | 0.04 | 86.70 | 0.79 | 0.87 | 10.89 | 0.61 | 0.08 | 90.50 | 87.43 | 79.13 |
| 9.9 | 450 | 0.25 | 209.7 | 0.04 | 86.66 | 0.78 | 0.76 | 11.03 | 0.64 | 0.08 | 91.64 | 87.22 | 79.93 |
| 9.9 | 450 | 0.25 | 220.0 | 0.05 | 86.72 | 0.77 | 0.52 | 11.11 | 0.77 | 0.07 | 94.32 | 85.57 | 80.71 |
| 9.9 | 450 | 0.25 | 220.3 | 0.07 | 87.17 | 0.76 | 0.39 | 10.71 | 0.86 | 0.06 | 95.76 | 83.80 | 80.25 |
| 9.9 | 450 | 0.25 | 220.0 | 0.07 | 87.09 | 0.73 | 0.35 | 10.83 | 0.91 | 0.06 | 96.21 | 83.42 | 80.26 |
| 9.9 | 450 | 0.25 | 230.0 | 0.09 | 87.30 | 0.73 | 0.23 | 10.61 | 1.05 | 0.05 | 97.54 | 81.24 | 79.24 |
| 9.9 | 450 | 0.25 | 230.0 | 0.10 | 86.34 | 1.04 | 0.16 | 11.11 | 1.28 | 0.05 | 98.21 | 79.32 | 77.90 |
| 9.9 | 450 | 0.25 | 230.0 | 0.12 | 87.88 | 0.67 | 0.13 | 10.07 | 1.20 | 0.04 | 98.61 | 78.55 | 77.46 |
| 9.9 | 450 | 0.25 | 240.0 | 0.14 | 87.71 | 0.69 | 0.09 | 9.95 | 1.51 | 0.03 | 98.99 | 74.66 | 73.90 |
| 9.9 | 450 | 0.25 | 240.0 | 0.17 | 88.37 | 0.66 | 0.06 | 9.27 | 1.56 | 0.03 | 99.29 | 71.97 | 71.46 |

TABLE 5

| H$_2$S/MeOH mole ratio | Press psig | WHSV | Temp ° C. | CO$_2$ Mol % | H$_2$S Mol % | H$_2$O Mol % | MeOH Mol % | MeSH Mol % | DMS Mol % | DMDS Mol % | MeOH Conversion % | MeSH Selectivity % | MeSH Yield % |
|---|---|---|---|---|---|---|---|---|---|---|---|---|---|
|  |  |  | Feed |  | 92.90 | 0.83 | 6.27 | 0 | 0 | 0 |  |  |  |
| 14.8 | 450 | 0.25 | 200.3 | 0.02 | 91.29 | 0.83 | 0.9 | 6.65 | 0.21 | 0.09 | 85.69 | 90.84 | 77.84 |
| 14.8 | 450 | 0.25 | 199.7 | 0.02 | 91.18 | 0.79 | 0.64 | 7.05 | 0.24 | 0.07 | 89.78 | 90.88 | 81.59 |
| 14.8 | 450 | 0.25 | 199.7 | 0.02 | 91.57 | 0.73 | 0.43 | 6.95 | 0.24 | 0.06 | 93.18 | 91.29 | 85.07 |
| 14.8 | 450 | 0.25 | 209.7 | 0.02 | 91.21 | 0.71 | 0.28 | 7.42 | 0.3 | 0.05 | 95.53 | 90.42 | 86.38 |
| 14.8 | 450 | 0.25 | 209.7 | 0.03 | 91.42 | 0.66 | 0.22 | 7.31 | 0.32 | 0.05 | 96.56 | 90.00 | 86.90 |
| 14.8 | 450 | 0.25 | 209.7 | 0.03 | 91.39 | 0.69 | 0.17 | 7.34 | 0.33 | 0.05 | 97.23 | 89.83 | 87.35 |
| 14.8 | 450 | 0.25 | 220 | 0.04 | 90.85 | 0.85 | 0.07 | 7.73 | 0.44 | 0.04 | 98.94 | 88.05 | 87.12 |
| 14.8 | 450 | 0.25 | 220 | 0.05 | 91.47 | 0.73 | 0.05 | 7.26 | 0.44 | 0.04 | 99.23 | 87.63 | 86.95 |
| 14.8 | 450 | 0.25 | 220 | 0.05 | 91.41 | 0.8 | 0.02 | 7.27 | 0.45 | 0.04 | 99.66 | 87.34 | 87.05 |
| 14.8 | 450 | 0.25 | 229.7 | 0.06 | 91.55 | 0.67 | 0 | 7.2 | 0.55 | 0.03 | 100 | 85.44 | 85.44 |
| 14.8 | 450 | 0.25 | 230 | 0.08 | 91.84 | 0.63 | 0 | 6.92 | 0.58 | 0.03 | 100 | 84.26 | 84.26 |

TABLE 5-continued

| H$_2$S/MeOH mole ratio | Press psig | WHSV | Temp °C. | CO$_2$ Mol % | H$_2$S Mol % | H$_2$O Mol % | MeOH Mol % | MeSH Mol % | DMS Mol % | DMDS Mol % | MeOH Conversion % | MeSH Selectivity % | MeSH Yield % |
|---|---|---|---|---|---|---|---|---|---|---|---|---|---|
| 14.8 | 450 | 0.25 | 230 | 0.08 | 91.76 | 0.64 | 0 | 6.98 | 0.6 | 0.03 | 100 | 83.89 | 83.89 |
| 14.8 | 450 | 0.25 | 239.3 | 0.08 | 91.27 | 0.7 | 0 | 7.24 | 0.76 | 0.02 | 100 | 81.44 | 81.44 |
| 14.8 | 450 | 0.25 | 240 | 0.1 | 91.21 | 0.68 | 0 | 7.21 | 0.87 | 0.02 | 100 | 79.30 | 79.30 |
| 14.8 | 450 | 0.25 | 240.3 | 0.1 | 91.45 | 0.64 | 0 | 7.03 | 0.86 | 0.02 | 100 | 79.06 | 79.06 |

TABLE 6

| H$_2$S/MeOH mole ratio | Press psig | WHSV | Temp °C. | CO$_2$ Mol % | H$_2$S Mol % | H$_2$O Mol % | MeOH Mol % | MeSH Mol % | DMS Mol % | DMDS Mol % | MeOH Conversion % | MeSH Selectivity % | MeSH Yield % |
|---|---|---|---|---|---|---|---|---|---|---|---|---|---|
|  |  |  | Feed | 0.00 | 94.22 | 0.28 | 5.50 | 0.00 | 0.00 | 0.00 |  |  |  |
| 17.1 | 450 | 0.25 | 160.7 | 0.00 | 94.48 | 0.69 | 2.55 | 2.25 | 0.03 | 0.01 | 53.64 | 95.16 | 51.04 |
| 17.1 | 450 | 0.25 | 160.7 | 0.00 | 93.75 | 0.90 | 3.15 | 2.15 | 0.03 | 0.01 | 42.73 | 95.36 | 40.75 |
| 17.1 | 450 | 0.25 | 160.7 | 0.00 | 93.21 | 1.07 | 3.61 | 2.07 | 0.03 | 0.01 | 34.46 | 95.43 | 32.88 |
| 17.1 | 450 | 0.25 | 171.0 | 0.00 | 92.65 | 1.15 | 3.91 | 2.23 | 0.03 | 0.01 | 28.99 | 95.70 | 27.74 |
| 17.1 | 450 | 0.25 | 171.0 | 0.00 | 92.41 | 1.13 | 3.67 | 2.73 | 0.04 | 0.01 | 33.39 | 95.62 | 31.92 |
| 17.1 | 450 | 0.25 | 171.0 | 0.00 | 94.59 | 0.96 | 2.23 | 2.22 | 0.00 | 0.00 | 59.56 | 100.00 | 59.56 |
| 17.1 | 450 | 0.25 | 180.7 | 0.00 | 92.10 | 1.30 | 3.20 | 3.32 | 0.05 | 0.01 | 41.91 | 95.52 | 40.03 |
| 17.1 | 450 | 0.25 | 181.3 | 0.00 | 91.80 | 1.40 | 3.17 | 3.53 | 0.05 | 0.01 | 42.50 | 95.05 | 40.40 |
| 17.1 | 450 | 0.25 | 181.0 | 0.00 | 91.96 | 1.30 | 2.76 | 3.88 | 0.06 | 0.01 | 49.86 | 95.10 | 47.42 |
| 17.1 | 450 | 0.25 | 190.3 | 0.00 | 91.96 | 1.14 | 2.30 | 4.48 | 0.08 | 0.01 | 58.22 | 95.21 | 55.44 |
| 17.1 | 450 | 0.25 | 191.3 | 0.00 | 91.58 | 1.14 | 1.98 | 5.15 | 0.09 | 0.01 | 64.10 | 94.69 | 60.70 |
| 17.1 | 450 | 0.25 | 191.0 | 0.00 | 91.72 | 1.03 | 1.53 | 5.54 | 0.12 | 0.02 | 72.21 | 94.20 | 68.02 |
| 17.1 | 450 | 0.25 | 200.7 | 0.00 | 91.41 | 1.00 | 1.27 | 6.14 | 0.13 | 0.02 | 77.01 | 94.42 | 72.71 |
| 17.1 | 450 | 0.25 | 201.0 | 0.00 | 91.74 | 0.92 | 1.06 | 6.09 | 0.13 | 0.02 | 80.83 | 94.24 | 76.17 |
| 17.1 | 450 | 0.25 | 201.3 | 0.00 | 91.68 | 0.87 | 0.80 | 6.44 | 0.14 | 0.02 | 85.48 | 94.17 | 80.50 |
| 17.1 | 450 | 0.25 | 210.3 | 0.02 | 91.94 | 0.80 | 0.49 | 6.52 | 0.16 | 0.02 | 91.07 | 93.56 | 85.20 |
| 17.1 | 450 | 0.25 | 211.3 | 0.02 | 91.90 | 0.76 | 0.40 | 6.68 | 0.18 | 0.02 | 92.72 | 93.17 | 86.39 |
| 17.1 | 450 | 0.25 | 211.0 | 0.02 | 92.02 | 0.72 | 0.27 | 6.71 | 0.19 | 0.02 | 95.04 | 93.03 | 88.42 |
| 17.1 | 450 | 0.25 | 221.0 | 0.04 | 92.47 | 0.65 | 0.02 | 6.55 | 0.21 | 0.02 | 99.62 | 92.18 | 91.83 |
| 17.1 | 450 | 0.25 | 221.3 | 0.05 | 92.18 | 0.73 | 0.00 | 6.75 | 0.24 | 0.02 | 100 | 91.48 | 91.48 |
| 17.1 | 450 | 0.25 | 220.7 | 0.05 | 91.14 | 0.67 | 0.00 | 7.76 | 0.33 | 0.02 | 100 | 90.49 | 90.49 |
| 17.1 | 450 | 0.25 | 230.7 | 0.05 | 91.60 | 0.67 | 0.00 | 7.33 | 0.31 | 0.01 | 100 | 90.81 | 90.81 |
| 17.1 | 450 | 0.25 | 231.3 | 0.06 | 92.05 | 0.64 | 0.00 | 6.90 | 0.32 | 0.01 | 100 | 90.04 | 90.04 |
| 17.1 | 450 | 0.25 | 231.3 | 0.07 | 91.86 | 0.66 | 0.00 | 7.02 | 0.38 | 0.01 | 100 | 89.24 | 89.24 |
| 17.1 | 450 | 0.25 | 241.3 | 0.08 | 91.99 | 0.66 | 0.00 | 6.85 | 0.41 | 0.01 | 100 | 88.04 | 88.04 |
| 17.1 | 450 | 0.25 | 241.3 | 0.09 | 91.78 | 0.67 | 0.00 | 6.97 | 0.48 | 0.01 | 100 | 86.73 | 86.73 |
| 17.1 | 450 | 0.25 | 241.3 | 0.10 | 92.31 | 0.68 | 0.00 | 6.42 | 0.48 | 0.01 | 100 | 85.57 | 85.57 |

TABLE 7

| Temperature (° F.) | 399 | 405 | 416 | 421 |
|---|---|---|---|---|
| Propylene WHSV | 0.68 | 0.71 | 0.64 | 0.62 |
| H$_2$S: propylene | 8.8 | 9.1 | 9.3 | 10.1 |
| Pressure (psig) | 330 | 330 | 330 | 330 |
| IPM mol % | 77.6 | 78.4 | 73.8 | 74.2 |
| NPM mol % | 9.4 | 9.0 | 10.1 | 11.3 |
| Unreacted propylene mol % | 1.0 | 1.2 | 0.9 | 0.4 |
| Heavies (sulfides) mol % | 10.6 | 10.4 | 8.8 | 12.0 |
| Mercaptans (IPM + NPM) | 87.0 | 87.4 | 84.9 | 85.5 |

TABLE 8

| Temperature (° F.) | 395 | 380 | 375 | 370 | 365 |
|---|---|---|---|---|---|
| IPM mol % | 73.6 | 85.1 | 85.1 | 88.2 | 88.0 |
| NPM mol % | 17.5 | 9.6 | 10.5 | 8.0 | 6.0 |
| Heavies (sulfides) mol % | 7.2 | 4.4 | 3.5 | 3.0 | 4.8 |

TABLE 9

| Temperature (° F.) | 373 | 372 | 374 |
|---|---|---|---|
| Propylene WHSV | 0.81 | 0.86 | 0.93 |
| H$_2$S: propylene | 7.4 | 6.8 | 6.5 |
| Pressure (psig) | 330 | 330 | 330 |

TABLE 9-continued

| IPM mol % | 86.0 | 86.5 | 84.7 |
|---|---|---|---|
| NPM mol % | 5.3 | 6.0 | 6.9 |
| Unreacted propylene mol % | <0.1 | 0.1 | 0.1 |
| Heavies (sulfides) mol % | 5.5 | 6.2 | 7.4 |
| Mercaptans (IPM + NPM) | 91.3 | 92.5 | 91.6 |

TABLE 10

| Example | 5A | 5B | 6 |
|---|---|---|---|
| SBM wt. % | 73.7 | 69.5 | 81.2 |
| NBM wt. % | 10.0 | 10.0 | 6.8 |
| Heavies (sulfides) wt. % | 8.7 | 11.6 | 6.6 |
| 1-Butene wt. % | 6.2 | 6.6 | 5.4 |
| Mercaptans wt. % | 83.7 | 79.5 | 87.8 |
| Temp (° F.) | 404.4 | 404.7 | 371.5 |
| Pressure (psig) | 330 | 330 | 330 |
| WHSV (1-butene) | 0.85 | 0.70 | 1.0 |
| Molar Feed Ratio | 6.0 | 7.7 | 4.2 |

TABLE 11

| Time (hour) | H$_2$S Feed (lb/min) | Pre-Heat Temp (° F.) | Reactor Inlet (° F.) | Reactor Outlet (° F.) | Reaction Pressure (psig) | WHSV (hr$^{-1}$) | Sulfiding Temp (° F.) |
|---|---|---|---|---|---|---|---|
| 9:00 | 0.2 | 38.2 | 43.9 | 37.6 | 2.3 | 0.0 | 41.4 |
| 10:00 | 0.4 | 41.5 | 51.6 | 44.8 | 2.5 | 0.0 | 49.3 |
| 11:00 | 20.8 | 246.0 | 92.8 | 283.5 | 154.7 | 1.6 | 184.3 |
| 12:00 | 13.8 | 211.4 | 157.4 | 194.2 | 130.9 | 1.0 | 171.4 |
| 13:00 | 14.0 | 243.4 | 126.4 | 140.2 | 109.7 | 1.1 | 136.8 |
| 14:00 | 116.0 | 212.2 | 158.8 | 130.1 | 121.8 | 8.7 | 141.0 |
| 15:00 | 139.6 | 307.6 | 191.5 | 123.9 | 110.3 | 10.5 | 156.0 |
| 16:00 | 56.1 | 311.9 | 213.2 | 124.7 | 107.1 | 4.2 | 167.9 |
| 17:00 | 10.3 | 297.7 | 197.3 | 119.0 | 98.8 | 0.8 | 155.7 |
| 18:00 | 88.3 | 316.0 | 195.9 | 118.7 | 99.3 | 6.6 | 155.7 |
| 19:00 | 88.7 | 326.2 | 205.8 | 120.7 | 114.5 | 6.7 | 161.4 |
| 20:00 | 111.7 | 324.9 | 212.4 | 119.7 | 210.9 | 8.4 | 164.2 |
| 21:00 | 143.3 | 317.1 | 209.7 | 122.4 | 141.2 | 10.8 | 161.8 |
| 22:00 | 14.8 | 302.3 | 187.0 | 112.5 | 233.5 | 1.1 | 142.9 |
| 23:00 | 0.7 | 202.7 | 109.3 | 71.2 | 246.5 | 0.1 | 88.9 |
| 0:00 | 0.6 | 167.0 | 77.7 | 67.1 | 239.3 | 0.0 | 70.4 |
| 1:00 | 0.5 | 143.0 | 66.6 | 65.8 | 237.7 | 0.0 | 64.9 |
| 2:00 | 0.4 | 129.6 | 63.3 | 63.4 | 231.1 | 0.0 | 61.0 |
| 3:00 | 0.3 | 130.4 | 62.4 | 61.9 | 228.0 | 0.0 | 58.5 |
| 4:00 | 0.2 | 127.8 | 61.5 | 60.5 | 224.6 | 0.0 | 55.8 |
| 5:00 | 0.1 | 121.4 | 60.6 | 60.3 | 224.2 | 0.0 | 54.8 |
| 6:00 | 0.0 | 120.8 | 59.8 | 59.8 | 222.2 | 0.0 | 54.3 |
| 7:00 | 0.0 | 118.2 | 59.7 | 59.8 | 223.5 | 0.0 | 54.9 |

TABLE 12

| Example | 8 | 9 |
|---|---|---|
| Ethyl mercaptan wt. % | 91.5 | 97.1 |
| Unreacted ethylene wt. % | 3.5 | <0.1 |
| Diethyl sulfide wt. % | 2.8 | 2.1 |
| Diethyl disulfide wt. % | 2.2 | 0.7 |
| Temp (° C.) | 242 | 199 |
| Pressure (bar) | 27 | 27 |
| WHSV (ethylene) | 0.73 | 0.71 |
| Molar Feed Ratio | 5.1 | 5.2 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for producing a mercaptan compound, the process comprising:
 (i) contacting a nickel-molybdenum catalyst with H$_2$S at a sulfiding temperature of less than or equal to about 235° C. to form a supported sulfur-containing catalyst; and
 (ii) contacting an alcohol compound, H$_2$S, and the supported sulfur-containing catalyst to form a reaction mixture comprising the mercaptan compound.

Aspect 2. A process for producing a mercaptan compound, the process comprising:
 (i) contacting a nickel-molybdenum catalyst with H$_2$S at a sulfiding temperature of less than or equal to about 235° C. to form a supported sulfur-containing catalyst; and
 (ii) contacting an olefin compound, H$_2$S, and the supported sulfur-containing catalyst to form a reaction mixture comprising the mercaptan compound.

Aspect 3. The process defined in aspect 1, wherein:
the mercaptan compound has formula (A): R$^1$—SH;
the alcohol compound has formula (B): R$^1$—OH; and
R$^1$ is a C$_1$ to C$_{18}$ substituted or unsubstituted, cycloalkyl group or linear or branched alkyl group.

Aspect 4. The process defined in aspect 2, wherein:
the mercaptan compound has formula (C): R$^2$—SH;
the olefin compound has the formula C═C or formula (D): R$^1$—C═C;
R$^1$ is a C$_1$ to C$_{18}$ substituted or unsubstituted, cycloalkyl group or linear or branched alkyl group; and
R$^2$ is a C$_3$ to C$_{20}$ substituted or unsubstituted, cycloalkyl group or linear or branched alkyl group.

Aspect 5. The process defined in any one of the preceding aspects, further comprising, prior to step (i), a step of contacting the nickel-molybdenum catalyst with an inert gas at a purging temperature of less than or equal to about 235° C.

Aspect 6. The process defined in aspect 5, wherein the inert gas comprises any suitable inert gas or any inert gas disclosed herein, e.g., helium, neon, argon, nitrogen, etc., or any combination thereof.

Aspect 7. The process defined in aspect 5 or 6, wherein the purging temperature is any suitable purging temperature or a temperature in any range disclosed herein, e.g., from about 60° C. to about 200° C., from about 110° C. to about 160° C., etc.

Aspect 8. The process defined in any one of the preceding aspects, wherein the sulfiding temperature is any suitable sulfiding temperature or a temperature in any range disclosed herein, e.g., from about 60° C. to about 200° C., from about 40° C. to about 100° C., from about 110° C. to about 160° C., etc.

Aspect 9. The process defined in any one of the preceding aspects, wherein step (i) comprises contacting the nickel-molybdenum catalyst with inlet H$_2$S at an inlet sulfiding temperature from about 10° C. to about 90° C., from about 35° C. to about 70° C., etc.

Aspect 10. The process defined in any one of the preceding aspects, wherein step (i) is conducted at any suitable sulfiding pressure or a pressure in any range disclosed herein, e.g., from about 50 to about 250 psig, from about 100 to about 150 psig, etc.

Aspect 11. The process defined in any one of the preceding aspects, wherein the nickel-molybdenum catalyst and the supported sulfur-containing catalyst contain any suitable amount of nickel or an amount in any range disclosed herein, e.g., from about 1 to about 5 wt. %, from about 1 to about 3 wt. %, from about 2 to about 5 wt. %, from about 2 to about 4 wt. %, from about 2.5 to about 4 wt. % nickel, etc., based on the total weight of the respective catalyst.

Aspect 12. The process defined in any one of the preceding aspects, wherein the nickel-molybdenum catalyst and the supported sulfur-containing catalyst contain any suitable amount of molybdenum or an amount in any range disclosed herein, e.g., from about 4 to about 18 wt. %, from about 4 to about 16 wt. %, from about 10 to about 15 wt. %, from about 11 to about 17 wt. %, from about 13 to about 16 wt. % molybdenum, etc., based on the total weight of the respective catalyst.

Aspect 13. The process defined in any one of the preceding aspects, wherein the supported sulfur-containing catalyst contains any suitable amount of sulfur or an amount in any range disclosed herein, e.g., from about 3 to about 18 wt. %, from about 4 to about 17 wt. %, from about 5 to about 15 wt. %, from about 7 to about 13 wt. % sulfur, etc., based on the total weight of the catalyst.

Aspect 14. The process defined in any one of the preceding aspects, wherein the nickel-molybdenum catalyst and the supported sulfur-containing catalyst contain any suitable amount of carbon or an amount in any range disclosed herein, e.g., less than or equal to about 3 wt. %, less than or equal to about 2.5 wt. %, less than or equal to about 2 wt. %, less than or equal to about 1 wt. %, less than or equal to about 0.5 wt. % carbon, etc., based on the total weight of the respective catalyst.

Aspect 15. The process defined in any one of the preceding aspects, wherein the nickel-molybdenum catalyst and the supported sulfur-containing catalyst comprise a solid support comprising any suitable solid support or any disclosed herein, e.g., silica, alumina (e.g., γ-alumina), magnesia, boria, titania, zirconia, a zeolite, etc., or a mixed oxide thereof, or a mixture thereof.

Aspect 16. The process defined in any one of the preceding aspects, wherein the nickel-molybdenum catalyst and the supported sulfur-containing catalyst are characterized by any suitable BET surface area or any BET surface area disclosed herein, e.g., from about 100 to about 300 m$^2$/g, from about 125 to about 275 m$^2$/g, from about 150 to about 250 m$^2$/g, etc.

Aspect 17. The process defined in any one of the preceding aspects, wherein the nickel-molybdenum catalyst and the supported sulfur-containing catalyst are in any suitable shape or form or any shape or form disclosed herein, e.g., powder, round or spherical (e.g., spheres), ellipsoidal, pellet, bead, cylinder, granule (e.g., regular and/or irregular), trilobe, quadralobe, ring, wagonwheel, monolith, etc., or any combination thereof.

Aspect 18. The process defined in any one of the preceding aspects, wherein the nickel-molybdenum catalyst and the supported sulfur-containing catalyst are characterized by any suitable average particle size (or average diameter) or any average particle size (or average diameter) disclosed herein, e.g., from about 0.5 to about 15 mm, from about 1 to about 7 mm, from about 2.5 to about 5 mm, etc.

Aspect 19. The process defined in any one of aspects 3-18, wherein $R^1$ and $R^2$ are branched alkyl groups.

Aspect 20. The process defined in any one of aspects 3-18, wherein $R^1$ and $R^2$ are linear alkyl groups.

Aspect 21. The process defined in any one of aspects 3-20, wherein $R^1$ and $R^2$ are substituted alkyl groups (e.g., a phenyl-substituted alkyl group).

Aspect 22. The process defined in any one of aspects 3-21, wherein $R^1$ is a $C_1$ to $C_{12}$ alkyl group.

Aspect 23. The process defined in any one of aspects 3-18, wherein $R^1$ is a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a cyclopentyl group, or a cyclohexyl group.

Aspect 24. The process defined in any one of aspects 3-18, wherein $R^1$ is a methyl group, an ethyl group, a propyl group, or a butyl group.

Aspect 25. The process defined in any one of aspects 3-18, wherein $R^1$ is a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, or a tert-amyl group.

Aspect 26. The process defined in any one of aspects 1-18, wherein the mercaptan compound is methyl mercaptan, ethyl mercaptan, isopropyl mercaptan, or sec-butyl mercaptan.

Aspect 27. The process defined in any one of the preceding aspects, wherein the process comprises combining the alcohol compound (or the olefin compound) with $H_2S$ prior to contacting the supported sulfur-containing catalyst.

Aspect 28. The process defined in any one of the preceding aspects, wherein step (ii) is conducted at a temperature in any suitable range or any range disclosed herein, e.g., from about 100° C. to about 300° C., from about 175° C. to about 275° C., from about 200° C. to about 250° C., etc.

Aspect 29. The process defined in any one of the preceding aspects, wherein step (ii) is conducted at a pressure in any suitable range or any range disclosed herein, e.g., from about 50 to about 1000 psig, from about 100 to about 800 psig, from about 150 to about 450 psig, etc.

Aspect 30. The process defined in any one of the preceding aspects, wherein a molar ratio of $H_2S$:alcohol compound (or $H_2S$:olefin compound) is in any suitable range or any range disclosed herein, e.g., from about 3:1 to about 10:1, from about 4:1 to about 30:1, from about 5:1 to about 20:1, from about 10:1 to about 15:1, etc.

Aspect 31. The process defined in any one of the preceding aspects, wherein the process comprises contacting the alcohol compound (or the olefin compound) and $H_2S$ with a fixed bed of the supported sulfur-containing catalyst.

Aspect 32. The process defined in any one of the preceding aspects, wherein step (ii) is conducted at any suitable WHSV or a WHSV in any range disclosed herein, e.g., from about 0.01 to about 3, from about 0.05 to about 1.5, from about 0.2 to about 1, etc.

Aspect 33. The process defined in any one of the preceding aspects, wherein the conversion of the alcohol compound or the olefin compound (or the yield to the mercaptan compound) is any molar percent conversion (or molar yield) disclosed herein, e.g., at least about 50%, at least about 60%, at least about 70%, at least about 80%, at least about 90%, etc.

Aspect 34. The process defined in any one of the preceding aspects, wherein the single pass conversion of the alcohol compound or the olefin compound (or the single pass yield to the mercaptan compound) is any single pass molar percent conversion (or single pass molar yield) disclosed herein, e.g., at least about 40%, at least about 50%, at least about 60%, at least about 70%, at least about 80%, etc.

Aspect 35. The process defined in any one of the preceding aspects, wherein the reaction mixture contains less than or equal to about 15 mol % of non-mercaptan reaction products (e.g., sulfides), less than or equal to about 10 mol % of non-mercaptan reaction products, less than or equal to about 5 mol % of non-mercaptan reaction products, etc.

Aspect 36. The process defined in any one of the preceding aspects, wherein the selectivity of the mercaptan compound is any selectivity disclosed herein, e.g. at least about 75 mol %, at least about 80 mol %, at least about 85 mol %, at least about 90 mol %, at least about 95 mol %, etc., based on the total mercaptan compounds in the reaction mixture.

Aspect 37. The process defined in any one of the preceding aspects, further comprising a step of isolating the mercaptan compound from the reaction mixture using any suitable technique or any technique disclosed herein, e.g., extraction, filtration, evaporation, distillation, etc., or any combination thereof, to form a product stream containing the mercaptan compound.

Aspect 38. The process defined in any one of the preceding aspects, wherein unreacted alcohol compound (or unreacted olefin compound) is recycled after step (ii).

We claim:

1. A process for producing a mercaptan compound, the process comprising:
    (i) contacting a nickel-molybdenum catalyst with inlet $H_2S$ at an inlet sulfiding temperature from about 10° C. to about 90° C. and sulfiding the nickel-molybdenum catalyst with $H_2S$ at a sulfiding temperature of less than or equal to about 235° C. to form a supported sulfur-containing catalyst; and
    (ii) contacting an alcohol compound or an olefin compound, $H_2S$, and the supported sulfur-containing catalyst to form a reaction mixture comprising the mercaptan compound.

2. The process of claim 1, wherein:
    the alcohol compound, $H_2S$, and the supported sulfur-containing catalyst are contacted in step (ii);
    the mercaptan compound has formula (A): $R^1$—SH;
    the alcohol compound has formula (B): $R^1$—OH; and
    $R^1$ is a $C_1$ to $C_{18}$ substituted or unsubstituted, cycloalkyl group or linear or branched alkyl group.

3. The process of claim 1, wherein:
    the olefin compound, $H_2S$, and the supported sulfur-containing catalyst are contacted in step (ii);
    the mercaptan compound has formula (C): $R_2$—SH;
    the olefin compound has the formula $H_2C$=$CH_2$ or formula (D): $R^1$—CH=$CH_2$;
    $R^1$ is a $C_1$ to $C_{18}$ substituted or unsubstituted, cycloalkyl group or linear or branched alkyl group; and
    $R^2$ is a $C_3$ to $C_{20}$ substituted or unsubstituted, cycloalkyl group or linear or branched alkyl group.

4. The process of claim 1, wherein:
    the alcohol compound comprises methanol, ethanol, a propanol, a butanol, a pentanol, a hexanol, a heptanol, an octanol, a nonanol, a decanol, an undecanol, a dodecanol, a tridecanol, a tetradecanol, a pentadecanol, a hexadecanol, a heptadecanol, an octadecanol, cyclopentanol, cyclohexanol, or any combination thereof; and
    the olefin compound comprises ethylene, propylene, a butene, a pentene, a hexene, a heptene, an octene, a decene, a dodecene, a tetradecene, a hexadecene, an octadecene, cyclopentene, cyclohexene, or any combination thereof.

5. The process of claim 1, wherein the mercaptan compound is methyl mercaptan, ethyl mercaptan, isopropyl mercaptan, or sec-butyl mercaptan.

6. The process of claim 1, wherein step (i) is conducted at:
    a sulfiding temperature from about 60° C. to about 200° C.; and
    a sulfiding pressure from about 50 to about 250 psig.

7. The process of claim 1, wherein the inlet sulfiding temperature is from about 20° C. to about 80° C.

8. The process of claim 1, wherein step (ii) is conducted at:
    a temperature in a range from about 100° C. to about 300° C.;
    a pressure in a range from about 50 to about 1000 psig; and
    a WHSV in a range from about 0.01 to about 3.

9. The process of claim 1, wherein step (ii) comprises contacting the alcohol compound or the olefin compound and $H_2S$ with a fixed bed of the supported sulfur-containing catalyst.

10. The process of claim 1, wherein a molar ratio of $H_2S$:alcohol compound or $H_2S$:olefin compound is in a range from about 3:1 to about 30:1.

11. The process of claim 1, further comprising, prior to step (i), a step of contacting the nickel-molybdenum catalyst with an inert gas at a purging temperature of less than or equal to about 235° C.

12. The process of claim 11, wherein:
    the inert gas comprises nitrogen; and
    the purging temperature is from about 60° C. to about 200° C.

13. The process of claim 1, wherein:
    a yield to the mercaptan compound is at least about 50 mol %; and/or
    a conversion of the alcohol compound or the olefin compound is at least about 50 mol %.

14. The process of claim 1, wherein the reaction mixture contains less than or equal to about 10 mol % of non-mercaptan reaction products.

15. The process of claim 1, wherein a selectivity of the mercaptan compound is at least about 80 mol %, based on the total mercaptan compounds in the reaction mixture.

16. The process of claim 1, further comprising a step of isolating the mercaptan compound from the reaction mixture to form a product stream containing the mercaptan compound.

17. The process of claim 1, wherein unreacted alcohol compound or unreacted olefin compound is recycled after step (ii).

18. The process of claim 1, wherein the nickel-molybdenum catalyst and the supported sulfur-containing catalyst independently comprise:
    a solid support;
    from about 1 to about 5 wt. % nickel; and
    from about 4 to about 18 wt. % molybdenum.

19. The process of claim 18, wherein the nickel-molybdenum catalyst and the supported sulfur-containing catalyst independently contain less than or equal to about 3 wt. % carbon.

20. The process of claim 18, wherein the nickel-molybdenum catalyst and the supported sulfur-containing catalyst independently are characterized by a BET surface area from about 100 to about 300 $m^2$/g.

21. The process of claim 18, wherein the supported sulfur-containing catalyst contains from about 3 to about 18 wt. % sulfur.

22. The process of claim 18, wherein the solid support comprises silica, alumina, magnesia, boria, titania, zirconia, a zeolite, a mixed oxide thereof, or a mixture thereof.

* * * * *